United States Patent [19]

Sohara et al.

[11] Patent Number: 5,089,652
[45] Date of Patent: Feb. 18, 1992

[54] NITRATE ESTER PREPARATION

[75] Inventors: Joseph A. Sohara, Walnutport; Randal A. Johnson, Hamburg; William E. Gorton, Allentown, all of Pa.

[73] Assignee: Atlas Powder Company, Dallas, Tex.

[21] Appl. No.: 466,221

[22] Filed: Jan. 17, 1990

[51] Int. Cl.$^5$ ............................................. C07C 205/00
[52] U.S. Cl. .................................... 558/480; 558/482; 558/483; 558/484; 558/485; 558/486
[58] Field of Search ............... 558/480, 482, 483, 484, 558/485, 486

[56] References Cited

U.S. PATENT DOCUMENTS

| | | | |
|---|---|---|---|
| 541,899 | 7/1895 | Thieme | 558/484 X |
| 879,899 | 2/1908 | Du Pont | 558/484 |
| 1,206,223 | 11/1916 | Hough | 558/484 |
| 1,371,215 | 3/1921 | Barab | 558/485 |
| 1,426,313 | 8/1922 | Oehme | 558/484 |
| 1,660,651 | 2/1928 | Marshall | 558/485 |
| 1,852,041 | 4/1932 | Crater | 558/486 |
| 1,868,388 | 7/1932 | Hough | 558/484 |
| 1,901,003 | 3/1933 | Schmid | 558/486 |
| 1,912,399 | 6/1933 | Norton et al. | 558/486 |
| 1,936,020 | 11/1933 | Hough | 558/484 |
| 2,225,893 | 12/1940 | Vanderbilt | 558/487 |
| 2,254,352 | 9/1941 | Cloud et al. | 558/480 |
| 2,294,592 | 9/1942 | Wyler | 558/487 |
| 2,389,228 | 11/1945 | Wyler | 558/487 |
| 2,461,582 | 2/1949 | Wright et al. | 260/467 |
| 2,485,855 | 10/1949 | Blomquist et al. | 260/467 |
| 2,678,946 | 5/1954 | Blomquist et al. | 260/467 |
| 2,957,021 | 10/1960 | Krantz | 558/487 |
| 2,978,484 | 4/1961 | Plant | 558/487 |
| 3,000,928 | 9/1961 | Frankel | 558/487 |
| 3,423,256 | 1/1969 | Griffith | 149/2 |
| 3,711,345 | 1/1973 | Tomic | 149/22 |
| 3,899,374 | 8/1975 | Sylkhouse | 149/2 |
| 4,352,699 | 10/1982 | Zeigler, Jr. | 149/109.6 |
| 4,371,408 | 2/1983 | Fillman | 149/21 |
| 4,381,958 | 5/1983 | Howard | 149/19.8 |
| 4,383,873 | 5/1983 | Wade et al. | 149/2 |
| 4,450,110 | 5/1984 | Simmons et al. | 260/349 |
| 4,457,791 | 7/1984 | Gill et al. | 149/19.3 |
| 4,522,756 | 6/1985 | Schack et al. | 260/349 |
| 4,523,967 | 6/1985 | Cartwright | 149/2 |
| 4,664,729 | 5/1987 | Rehman | 149/21 |
| 4,726,919 | 2/1988 | Kristofferson et al. | 264/33 |
| 4,761,250 | 8/1988 | Frankel et al. | 260/349 |
| 4,853,157 | 8/1989 | Stiff | 558/483 |

FOREIGN PATENT DOCUMENTS 0129995  2/1985  European Pat. Off. .

OTHER PUBLICATIONS

U.S. Statutory Invention Registration No. H448 to Farncomb, et al., published Mar. 1, 1988, filed Jul. 6, 1988.

"Zeitschrift fur das gesamte Schiefb und Sprengstoffwesen," *Investigation of Extraction and Characteristics of Nitrostarches* (and English translation thereof) by J. Hackel and T. Urbanski, Warsaw, Poland, Oct. 1933, Issue Nos. 10, 11, 12.

*Primary Examiner*—Robert L. Stoll
*Assistant Examiner*—Chhaya Sayala
*Attorney, Agent, or Firm*—Richards, Medlock & Andrews

[57] ABSTRACT

The process of the present invention provides a method of obtaining a high yield of water or acid soluble nitrate esters without the use of organic solvents in the nitration reaction or the production of unstable products or by-products. The process involves the nitration of an organic hydroxy-containing compound with a suitable nitrating agent such as nitric acid in the absence of organic solvents in the nitration reaction. The reaction mixture is neutralized, causing the nitrate esters to precipitate or separate from the neutralized nitrate solution. The nitrate ester is then recovered, and any dissolved nitrate salts can be removed therefrom by gentle washing with water or a dilute halide solution. As provided by the process of the present invention, no organic solvents are used in the nitration reaction and average yields range from about 80% to about 95%.

31 Claims, No Drawings

NITRATE ESTER PREPARATION

TECHNICAL FIELD OF THE INVENTION

The present invention relates to a method of preparing nitrate esters from the nitration of organic hydroxy-containing compounds with nitric acid wherein no organic solvents are utilized in the nitration reaction.

BACKGROUND OF THE INVENTION

Methods for the production of nitrate esters are known and are in commercial use. The known methods utilize strong nitric acid or admixtures of nitric acid with sulfuric acid and/or acetic acid to nitrate the appropriate hydroxy-containing organic substance. Typically, such mixed acid systems have been used because they provide enhanced yields and chemical efficiency. Mixed acid nitration media are often used to produce high $NO_2^+$ concentrations in order to achieve complete nitration. High $NO_2^+$ concentrations are reported to occur when essentially equal molar amounts of nitric acid and sulfuric acid are utilized. As reported by Urbansky, the production of unwanted by-products increases as the amount of secondary acid is reduced or eliminated. Urbansky further reports that the yield of desired product decreases as the amount of nitric acid is reduced. The resulting nitrate ester produced from the above-described processes is usually insoluble in the spent acid solution and thus forms an immiscible layer of product and/or a solid precipitate. The product and the spent acid solution are both relatively stable after separation.

However, some commercially desirable nitrate esters are soluble in the spent acid solution. When the desired nitrated ester product is partially soluble in the spent acid solution, very low yields of the nitrate ester are obtained and the spent acid solution becomes very unstable, usually "fuming off" within a few minutes. The unstable spent acid solution admixture and/or product is due to the presence of mixtures of organic materials and oxidizing acid.

In the past, to alleviate the problem of producing the nitrate esters which prove to be soluble in the spent acid solution, an inert organic solvent has been added to the nitric acid or mixed acid medium in the nitration of the hydroxy-containing organic substance. An example of a process known in the chemical industry includes the method disclosed in European Patent Application No. 843037524. The chemistry of the reaction in that method necessitates the use of an organic solvent with the acid in the nitration medium. The use of an organic solvent with the acids in the nitrating medium causes the partially soluble nitrate esters to be extracted into the organic phase, which can then be separated and recovered, resulting in an increased yield of nitrate ester product. These organic solvents are chosen and used so as to be effective to remove the heretofore partially soluble nitrate esters from the acid phase, enhancing the recovery of the desired nitrate ester. Furthermore, these organic solvents are used in an amount effective to cause the complete extraction of nitrate esters into the organic phase. The organic solvent used must be insoluble in water, inert toward nitration, and volatile so that the product may be recovered. These restrictions limit the choice of solvents which can be utilized to halogenated aliphatic compounds, preferably chloroform and/or methylene chloride. Using these solvents in the nitration mixture will provide very high yields of clean, stable products and stable spent acid solutions. However, as set forth above, the only solvents which are inert to nitration, insoluble in water, and volatile are the halogenated aliphatic hydrocarbons, which are considered toxic or hazardous substances in many geographic locations. The use of these solvents requires special handling and treatment of all effluents and waste materials which come into contact with the solvent. Also, when such organic solvents are used in the nitration step, recovery of the final product requires the removal of the spent acid phase, wherein the spent acids are recovered either separately or as a mixed stream, followed by the separate step of neutralization of the product/solvent solution. Thereafter, the solvent must be removed in order to recover the nitrate ester product. Therefore, the use of such solvents substantially increases the cost of production of those nitrate esters which are somewhat soluble in the spent acid mixture. Furthermore, at the present time, there is some concern about the future availability of halogenated aliphatic hydrocarbon solvents such as methylene chloride.

Thus, there has been a need to provide a process by which high yields of water- or acid-soluble nitrate esters may be prepared without the use of organic solvents in the nitration reaction or the production of unstable products or by-products.

SUMMARY OF THE INVENTION

The process of the present invention provides for the production of nitrate esters. The process has been developed for the efficient production of nitrate esters especially those which are partially soluble in spent acid mixtures.

The process of the present invention provides for the nitration of hydroxy-containing compounds with an excess of a nitrating agent wherein no organic solvents are utilized in the nitration reaction. The nitration mixture is neutralized in situ, causing the nitrate esters to precipitate and thus separate from the neutralized solution. The stable nitrate ester product is then recovered and the dissolved nitrate salts can be removed therefrom by washing.

In one embodiment of the invention, the hydroxy-containing compound is contacted by an excess of nitrating agent in the absence of organic solvents under suitable reaction conditions to produce a reaction mixture of excess nitrating agent and at least one nitrate ester which is partially soluble in the spent acid of the reaction mixture. Thereafter, the reaction mixture is contacted with a suitable base to neutralize the excess nitrating agent to form a nitrate salt such that the nitrate ester is substantially insoluble in the neutralized mixture and may thereafter be isolated and recovered. In a preferred embodiment, the hydroxy-containing compound is contacted with nitric acid without the addition of organic solvents with cooling until the nitration reaction is complete. The reaction mixture is neutralized with an inorganic base, thus forming two phases, one of which contains the nitrate ester product. The nitrate ester may be isolated and washed to remove any dissolved inorganic salts. If desired, the nitrate ester product may be washed with acetone and/or sparged with gas to drive off water in the final product.

DETAILED DESCRIPTION

The process of the present invention is suitable for the production of esters from the nitration of hydroxy-containing compounds. Generally, the process provides for the production of nitrate esters from the nitration of hydroxy-containing compounds with an excess of nitrating agent wherein no organic solvents are utilized in the nitration reaction. The process of the present invention is particularly well suited for the production of nitrate esters which are at least partially soluble in the spent acid of the reaction mixture.

The process of the present invention produces a stable neutral waste nitrate solution which contains small amounts of nitrate ester product and by-products which are easily treated in normal facilities. The process of the present invention does not use toxic or hazardous organic solvents and average yields range from about 80% to about 95%.

Although the yield of product based on amount of starting material is sometimes lower than that produced by employing an organic solvent in the nitration reaction, the throughput, and hence the commercial value of this method, is great, because the process of the present invention is able to utilize a larger portion reactor volume for reactants. The standard known methods which employ an organic solvent in the nitration of the hydroxy-containing compound must necessarily fill a substantial part of the available reactor volume with an inert organic solvent, resulting in a large increase in the number of reactor volumes needed for the production of a fixed amount of nitrate ester product. Furthermore, the neutral waste stream produced by the present inventive process produces only easily treatable waste, some of which may be suitable without treatment for use in applications requiring nitrate salts.

Nitration can be effected by contacting the hydroxy-containing compound with a suitable nitrating agent, without the addition of organic solvents, under suitable reaction conditions. Generally, nitration is effected by contacting the hydroxy-containing compound with an excess of the nitrating agent. Preferably, the nitration is effected by the slow addition of the hydroxy-containing compound to an excess amount of nitric acid.

Suitable hydroxy-containing compounds include those having the formula $R-(OH)_x$ wherein R is an organic chain or ring, and x is in the range of 1 to 10 and preferably 1 to 4. R can be any hydrocarbon chain or ring, heterogeneous chain or ring, or substituted hydrocarbon chain or ring where the substituents do not interfere significantly with the nitration reaction. Substituents which have been found to substantially interfere with the nitration reaction include, for example, those having an amine, amide, or acid group and those substituents having a loosely attached hydrogen moiety. Hydrocarbon chains having 1 to 30 carbon atoms can be usefully employed, while those having 1 to 20 carbon atoms are preferred.

For the suitable production of nitrate esters utilizing the present process, an excess amount of nitrating agent should be used. Generally, at least two times the stoichiometric amount of nitrating agent per hydroxyl group to be nitrated should be added. A ratio of more than 8 moles of nitrating agent per mole of hydroxyl group generally does not provide any additional benefits. Preferably, four to six times the stoichiometric amount of nitric acid per mole of hydroxyl group to be nitrated should be used. For the nitration of polyethylene glycols, it has been determined that the amount of nitric acid necessary to maximize the yield of nitrate esters is approximately 500% of the stoichiometric amount, that is, about 5 molecules of nitric acid per molecule of hydroxyl group to be nitrated.

Nitric acid is a suitable nitrating agent for use in the present process. Other nitrating agents may be usefully employed, such as nitrogen pentoxide, as well as mixtures of nitric acid with sulfuric acid, phosphoric acid, or acetic acid. However, it is preferable to use nitric acid without another secondary acid because the spent acid solution produced when nitric acid is used alone produces a clean, stable and desirable by-product of sodium nitrate, which thereafter may be sold without substantial treatment. When a mixed acid nitrating medium is used, e.g. nitric acid and sulfuric acid, the resulting spent acid solution produces by-products containing nitrates mixed with undesirable sulfate by-products. Generally, the nitric acid should be strong nitric acid, that is, between about 92% and about 98%. Preferably, the nitric acid is about 96% to about 98%.

The reaction of the present process is exothermic. Therefore, the reaction temperature should be maintained within a suitable range by appropriate measures. Generally, the reaction temperature is maintained by controlling the rate of addition of the hydroxy-containing compound and/or by cooling. Preferably, the reaction temperature is maintained between about 0° C. and 10° C. by the above described methods. It is also preferable to maintain the reaction temperature between about 0° C. and 10° C. until the reaction is at least substantially complete. Preferably, an additional 5-10 minutes of agitation and cooling is desired to insure the completion of the reaction.

Of course, the conditions suitable for the reaction, including the amounts of reactants and temperatures, can be adjusted by experimentation to give the highest possible yield of nitrate ester product for each particular hydroxy-containing compound nitrated.

After the reaction is complete, the excess nitrating agent is neutralized in situ using a suitable base or is drowned into water. The reaction mixture may also be diluted with water while being cooled, then neutralized with a stronger suitable base. To maximize the yield of nitrate ester product, it is preferable to completely neutralize the excess acid. Preferably, the excess acid is neutralized through the addition of solid sodium carbonate or ammonia gas. Other inorganic compounds can be used to neutralize the mixture, such as sodium hydroxide, sodium bicarbonate, potassium hydroxide, potassium bicarbonate, and ammonium hydroxide.

After the neutralization of the excess acid, two liquid phases will form: an aqueous solution containing inorganic salts and an organic phase containing the nitrate ester product. The salt solution will have a different density than the phase containing the nitrate ester product, thus forming two phases. Generally, the nitrate salt solution will have a lower density than the phase containing the nitrate ester product. After neutralization, the nitrate ester product is neutral and can be separated from the nitrate salt solution. Generally, the separated organic phase containing the neutral nitrate ester product is washed to remove any dissolved nitrate salts. Typically, the wash is done with water or a very dilute aqueous salt solution.

With certain nitrate ester products, the washing with water may form an emulsion or dispersion. In such cases, it is preferable to wash the separated organic phase containing nitrate ester product with a very dilute solution of sodium chloride or similar compound to prevent the formation of an emulsion or dispersion.

Furthermore, in some instances, acetone or another volatile organic solvent may be added after neutralization to aid in the separation or precipitation of the dissolved salts and to aid in the removal of water from the product. The use of acetone assists in driving off water in those instances where the presence of water is not desirable in the final product. The use of acetone is not required, however, and any undesired water may be driven off by sparging the product with air or gas or by other suitable methods. Of course, the presence of water in the final nitrate ester product may be desirable, such as in the production of nitrostarch.

Generally, the resulting nitrate ester product will contain some water. If desired, the amount of water may be reduced through absorption techniques or by evaporation. The reduction of water in the product through the use of the above-described techniques will generally result in the precipitation of dissolved salts which may be removed by filtration or decantation of the product.

EXAMPLE 1

A charge of 260 grams of 96.7% nitric acid was cooled to 0° C., then the nitric acid was contacted with 80 grams of tetraethylene glycol with cooling to maintain a reaction temperature of 8° C. or lower. The nitration reaction was carried out in the absence of organic solvents. After the reaction was complete and the temperature had stabilized, approximately 600 grams of ice and water were added to the reaction mixture with cooling as necessary to keep the resulting temperature below 10° C. Solid sodium carbonate was then added to the reaction mixture with moderate stirring until the excess nitric acid was neutralized. An additional 160 grams of water was added to clear up the solution and the total mixture was transferred to a separatory funnel. The nitrate ester product separated to the bottom of the funnel and was drawn off.

The product was washed lightly with 60 grams of water yielding 108 grams of slightly milky product. The addition of 15 grams of acetone cleared the solution which was then heated to 80° C. and sparged with nitrogen to obtain the final product which, after filtration, yielded 98 grams of product (84% yield). The infrared spectrum identified the product as essentially pure tetraethylene glycol dinitrate and showed that it was free of solvent, unreacted starting material, or oxidized by-product.

EXAMPLE 2

A charge of 140.8 grams of 96.7% nitric acid was cooled to 0° C., then the nitric acid was contacted with 40.0 grams of tetraethylene glycol with cooling to maintain a reaction temperature of 8° C. or lower. The reaction was carried out in the absence of organic solvents. After the reaction was complete and the temperature had stabilized, 102 grams of water was added to the reaction mixture with cooling as necessary to keep the temperature below 10° C. Ammonia gas was then slowly bubbled through the resulting reaction mixture with cooling to neutralize the excess nitric acid. A milky product was separated from the neutralized reaction mixture yielding 50.7 grams of unpurified nitrate ester. The milky reaction product was further washed and purified by the steps as set forth in Example 1. Infrared analysis identified the product as tetraethylene glycol dinitrate and showed that it was free of solvent, unreacted starting material or oxidized by-product.

EXAMPLE 3

A suitable nitrate ester product could be obtained using the following hypothetical example. A charge of 260 grams of 96.7% nitric acid is to be cooled to 0° C. and then contacted with 80 grams of tetraethylene glycol with cooling to maintain a reaction temperature of 8° C. or lower. No organic solvents are to be added to the nitration reaction mixture. After the addition of the nitric acid, the nitration reaction is to be allowed to go to completion.

After the temperature of the reaction mixture has stabilized, approximately 600 grams of ice and water is to be added to the reaction mixture with cooling as may be necessary to maintain the resulting temperature below 10° C. Solid sodium carbonate is then added to the reaction mixture with moderate stirring until the excess nitric acid is neutralized. Thereafter, an additional 160 grams of water is to be added to the reaction mixture and the entire mixture is then transferred to a separatory funnel. The liquid phase containing the nitrate ester product will separate from the aqueous phase containing the nitrate salts, and thereafter, the liquid phase containing the nitrate ester product may be drawn off from the bottom of the separatory funnel. The phase containing the product is then to be lightly washed with 65 grams of water. The resulting product is then to be heated to 80° C. and sparged with nitrogen to drive off excess water contained in the product. The product is then to be filtered to obtain the final nitrate ester product.

One skilled in the art will recognize it is possible to make the compositions of this invention from a variety of materials and by a variety of slight variations of this process. While the preferred embodiments of the present invention have been described in detail, it will be evident that various further modifications are possible without departing from the scope of the invention.

We claim:

1. A method of preparing nitrate esters by the nitration of organic hydroxy-containing compounds comprising:
   (a) contacting an organic hydroxy-containing compound having the structure of $R—(OH)_x$ wherein R is an organic chain or ring having from about 1 to about 20 carbon atoms and not having an amine, amide or acid group or loosely attached hydrogen moiety substituent and x is in the range of about 1 to about 10 with a single nitrating agent, in the absence of an organic solvent effective to extract a partially soluble nitrate ester from the reaction mixture, under suitable reaction conditions to produce a reaction mixture of excess nitrating agent and at least one nitrate ester at least partially soluble in said reaction mixture; and
   (b) contacting said reaction mixture with a base to neutralize the excess nitrating agent to form a salt thereof such that said nitrate ester is substantially insoluble in the thus neutralized mixture.

2. The method of claim 1 further comprising the step of isolating said insoluble nitrate ester from the neutralized mixture.

3. A method in accordance with claim 1 wherein said nitrating agent is nitric acid.

4. A method in accordance with claim 1 wherein said nitrating agent is about 90% to about 98% nitric acid.

5. A method in accordance with claim 1 wherein said nitrating agent is present from about 2 to about 8 moles per mole of hydroxyl-group to be nitrated.

6. A method in accordance with claim 1 wherein said nitrating agent is present from about 4 to about 6 moles per mole of hydroxyl-group to be nitrated.

7. A method in accordance with claim 1 wherein R is selected from the group including hydrocarbon chains or rings or halogenated hydrocarbon chains or rings.

8. A method in accordance with claim 1 wherein R is selected from the group including aliphatics having from about 1 to about 10 carbon atoms, cycloaliphatics having from about 3 to about 10 carbon atoms, and aromatics having from about 6 to about 10 carbon atoms.

9. A method of preparing nitrate esters by the nitration of organic hydroxy-containing compounds comprising:
   (a) contacting an organic hydroxy-containing compound having the structure of R—$(OH)_x$ wherein R is an organic chain or ring having from about 1 to about 20 carbon atoms and not having an amine, amide or acid group or loosely attached hydrogen moiety substituent and x is in the range of about 1 to about 10 with nitric acid, in the absence of an organic solvent effective to extract a soluble nitrate ester from the acid phase, under suitable reaction conditions to produce a reaction mixture of excess nitric acid and at least one nitrate ester at least partially soluble in said mixture; and
   (b) contacting said reaction mixture with an alkali compound to neutralize the excess nitric acid to form a salt thereof such that said nitrate ester is substantially insoluble in the thus neutralized mixture.

10. The method of claim 9 further comprising isolating said insoluble nitrate ester from the neutralized mixture.

11. The method of claim 9 wherein said nitric acid is about 96% to about 98%.

12. The method of claim 9 wherein said nitric acid is present from about 2 to about 8 moles per mole of hydroxyl-group to be nitrated.

13. The method of claim 9 wherein said nitric acid is present from about 4 to about 6 moles of hydroxy-group to be nitrated.

14. The method of claim 9 wherein R is selected from the group including hydrocarbon chains or rings or halogenated substituted hydrocarbon chains or rings.

15. The method of claim 9 wherein R is selected from the group including aliphatics having from about 1 to about 10 carbon atoms, cycloaliphatics having from about 3 to about 10 carbon atoms, and aromatics having from about 6 to about 10 carbon atoms.

16. A method of preparing nitrate esters by the nitration of organic hydroxy-containing compounds consisting essentially of:
   (a) slowly adding an organic hydroxy-containing compound having the structure of R—$(OH)_x$ wherein R is an organic chain or ring having from about 1 to about 20 carbon atoms and not having an amine, amide or acid group or loosely attached hydrogen moiety substituent and x is in the range of about 1 to about 10 to an excess amount of nitric acid, in the absence of an organic solvent effective to extract a soluble nitrate ester from the acid phase, under suitable reaction conditions to produce a reaction mixture of excess nitric acid and at least one nitrate ester soluble in said reaction mixture; and
   (b) contacting said reaction mixture with an alkali compound to neutralize the excess nitric acid to form a salt thereof such that said nitrate ester is at least substantially insoluble in the thus neutralized mixture.

17. The method of claim 16 further comprising the step of isolating said insoluble nitrate ester from the neutralized mixture.

18. The method of claim 16 wherein said nitric acid is about 96% to about 98%.

19. The method of claim 16 wherein said organic hydroxy-containing compound is added to about 2 to about 8 moles of nitric acid per mole of hydroxyl-group to be nitrated.

20. The method of claim 16 wherein said organic hydroxy-containing compound is added to about 4 to about 6 moles of nitric acid per mole of hydroxyl-group to be nitrated.

21. The method of claim 16 wherein R is selected from the group including hydrocarbon chains or rings halogenated substituted hydrocarbon chains or rings.

22. The method of claim 16 wherein R is selected from the group including aliphatics having from about 1 to about 10 carbon atoms, cycloaliphatics having from about 3 to about 10 carbon atoms, and aromatics having from about 6 to about 10 carbon atoms.

23. A method of preparing nitrate esters by the nitration of alcohols consisting essentially of:
   (a) slowly adding an alcohol having the structure of R—$(OH)_x$ wherein R is an organic chain or ring having from about 1 to about 20 carbon atoms and not having an amine, amide or acid group or loosely attached hydrogen moiety substituent and x is in the range of about 1 to about 10 to an excess amount of concentrated nitric acid in the absence of an organic solvent effective to extract a soluble nitrate ester from the acid phase;
   (b) maintaining the temperature of the reaction mixture of step (a) between about 0° C. to about 10° C. until the reaction is complete;
   (c) agitating and maintaining the temperature of the thus completed reaction of step (b) for about 5 to about 10 minutes;
   (d) contacting said reaction mixture of step (c) with an alkali compound to neutralize the excess nitric acid and forming a nitrate salt thereof such that said nitrate esters are substantially insoluble in the thus neutralized mixture of step (d); and
   (e) isolating the insoluble nitrate esters from the neutralized nitrate salt solution.

24. The method of claim 23 wherein said nitric acid is about 96% to about 98%.

25. The method of claim 23 wherein said alcohol is added to about 2 to about 8 moles of nitric acid per mole of hydroxyl-group to be nitrated.

26. The method of claim 23 wherein said alcohol is added to about 4 to about 6 moles of nitric acid per mole of hydroxyl-group to be nitrated.

27. The method of claim 23 wherein R is selected from the group including hydrocarbon chains or rings or halogenated substituted hydrocarbon chains or rings.

28. The method of claim 23 wherein R is selected from the group including aliphatics having from about 1 to about 10 hydrocarbons, cycloaliphatics having from about 3 to about 10 carbon atoms and aromatics having from about 6 to about 10 carbon atoms.

29. The method of claim 23 wherein said alkali compound is a sodium carbonate solution.

30. The method of claim 23 further consisting of washing said isolated insoluble nitrate esters of step (e) with water.

31. The method of claim 23 further consisting of washing said isolated insoluble nitrate esters of step (e) with a dilute halide solution to prevent the formation of an emulsion.

* * * * *

UNITED STATES PATENT AND TRADEMARK OFFICE
CERTIFICATE OF CORRECTION

PATENT NO. : 5,089,652

DATED : February 18, 1992

INVENTOR(S) : Joseph A. Sohara, et al

It is certified that error appears in the above-identified patent and that said Letters Patent is hereby corrected as shown below:

Column 1, line 66-67, delete "and-/or" and insert therefor --and/or--.

Column 2, line 32, after "esters" insert --,--.
         line 39, delete "in situ," and insert therefor --<u>in situ</u>,--.

Column 4, line 26, delete "above described" and insert therefor
         --above-described--.
         line 38, delete "in situ" and insert therefore --<u>in situ</u>--.

Column 7, line 45, delete "hydroxy-" and insert therefor --hydroxyl--.

Column 4, line 13, delete "e.g." and insert therefor --<u>e.g.</u>--.

Signed and Sealed this

Tenth Day of August, 1993

Attest:

MICHAEL K. KIRK

Attesting Officer      Acting Commissioner of Patents and Trademarks